United States Patent
Kariya et al.

(10) Patent No.: US 8,845,954 B2
(45) Date of Patent: Sep. 30, 2014

(54) ZIRCONIA-BASED COMPOSITE CERAMIC SINTERED COMPACT AND METHOD FOR PRODUCING THE SAME

(75) Inventors: Shuji Kariya, Itabashi-ku (JP); Akio Takahashi, Itabashi-ku (JP); Go Mashio, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/435,541

(22) Filed: Mar. 30, 2012

(65) Prior Publication Data

US 2012/0252654 A1    Oct. 4, 2012

(30) Foreign Application Priority Data

Mar. 31, 2011    (JP) .................................. 2011-078770

(51) Int. Cl.
C04B 35/48 (2006.01)
C04B 35/626 (2006.01)
C04B 35/488 (2006.01)
A61C 13/083 (2006.01)

(52) U.S. Cl.
CPC ......... *C04B 35/6263* (2013.01); *C04B 35/6264* (2013.01); *C04B 2235/44* (2013.01); *C04B 2235/3229* (2013.01); *C04B 2235/765* (2013.01); *C04B 2235/3206* (2013.01); *C04B 2235/612* (2013.01); *C04B 2235/442* (2013.01); *C04B 2235/3224* (2013.01); *C04B 2235/444* (2013.01); *C04B 2235/3246* (2013.01); *C04B 2235/9661* (2013.01); *C04B 35/4885* (2013.01); *C04B 2235/3279* (2013.01); *A61C 13/083* (2013.01); *C04B 2235/3232* (2013.01); *C04B 2235/72* (2013.01)
USPC ......................................................... 264/655

(58) Field of Classification Search
USPC ....................................................... 264/655
See application file for complete search history.

(56) References Cited

U.S. PATENT DOCUMENTS

| | | | |
|---|---|---|---|
| 6,709,694 B1 * | 3/2004 | Suttor et al. | 427/2.26 |
| 8,034,264 B2 * | 10/2011 | Ritzberger et al. | 264/17 |
| 8,173,562 B2 * | 5/2012 | Holand et al. | 501/103 |
| 2008/0303181 A1 | 12/2008 | Holand et al. | |
| 2011/0236860 A1 * | 9/2011 | Jahns et al. | 433/222.1 |

FOREIGN PATENT DOCUMENTS

| | | |
|---|---|---|
| DE | 199 04 522 A1 | 8/2000 |
| EP | 0 218 853 A1 | 4/1987 |
| JP | 2002-536280 A | 10/2002 |
| JP | 2004-051481 A | 2/2004 |
| JP | 2004-059374 A | 2/2004 |
| JP | 2005-097094 A | 4/2005 |
| JP | 2005-306678 A | 11/2005 |
| JP | 2005-306726 A | 11/2005 |
| JP | 2006-271435 A | 10/2006 |
| JP | 2010-534245 A | 11/2010 |

OTHER PUBLICATIONS

Extended European Search Report dated Jul. 16, 2012, in European Patent Application No. 12 002 360.1-2111.

* cited by examiner

*Primary Examiner* — Joseph S Del Sole
*Assistant Examiner* — Russell Kemmerle, III
(74) *Attorney, Agent, or Firm* — Oblon, Spivak, McClelland, Maier & Neustadt, L.L.P.

(57) ABSTRACT

To provide a zirconia-based composite ceramic sintered compact capable of being colored to white appropriate for a dental prosthesis while maintaining its mechanical and physical properties, and also provide a method for producing the same. The method for producing the zirconia-based composite ceramic sintered compact includes semi-sintering a zirconia-alumina composite ceramic containing an alumina particle and a zirconia particle comprising of tetragonal zirconia containing ceria of 8 to 12 mol %, forming the composite ceramic; dipping the formed composite ceramic in a neodymium ion solution or complex solution; drying the dipped composite ceramic; and finally sintering it.

4 Claims, No Drawings

ZIRCONIA-BASED COMPOSITE CERAMIC SINTERED COMPACT AND METHOD FOR PRODUCING THE SAME

BACKGROUND OF THE INVENTION

1. Field of the Invention

The present invention relates to a zirconia-based composite ceramic sintered compact colored by a neodymium ion solution or a neodymium complex solution, and a method producing the same.

2. Description of the Conventional Art

Compared with metal materials or plastic materials, ceramic materials are excellent in hardness, wear resistance, heat resistance, corrosion resistance, and the like. In a dental field, ceramics materials, such as an alumina sintered compact being chemically stable, a zirconia sintered compact being excellent in strength and toughness, an alumina/zirconia composite sintered compact, and the like, are formed and processed to be a dental prosthesis by using CAD/CAM, and used clinically.

Zirconia has a monoclinic system at a room temperature, and a crystal structure of zirconia is phase-transited to a tetragonal system and then to a cubic system as increasing the temperature. Since the phase transition accompanies changing in volume, the sintered compact comes to be broken by repeatedly heating and cooling. Therefore, partially stabilized zirconia has been widely used. The partially stabilized zirconia is made by solid-dissolving rare-earth oxide, such as yttrium oxide, cerium oxide or the like, in zirconia as a stabilizer and forming oxygen vacancies in the crystal structure. The partially stabilized zirconia can suppress breaking of the sintered compact due to heating and cooling.

The yttrium-based partially stabilized zirconia in which yttrium oxide is solid-dissolved as a stabilizer is suitable for a dental prosthesis because of having a white color tone. However, since the tetragonal system which is a metastable phase is phase-transited to the monoclinic system at a comparatively low temperature (200 to 300° C.), there is a problem that cracks are generated inside due to volume expansion at the time of transformation so as to decrease strength. Furthermore, the phase transition is generated even at a low temperature of about 37° C. in such a wet environment as inside of an oral cavity, so that it has been pointed out that the surface is roughed or the strength decreases.

Further, the ceria-based partially stabilized zirconia in which cerium oxide is solid-dissolved as a stabilizer hardly deteriorates at low temperature and has high strength and toughness. As the ceria-based partially stabilized zirconia, a zirconia-alumina composite ceramic material consists of a first phase and a second phase has been disclosed (for example, refer to Japanese Patent Application Laid-Open Nos. 2004-051481, 2005-097094, 2005-306726, and 2006-271435). In the zirconia-alumina composite ceramic material, the first phase includes a $ZrO_2$ particle including ceria of 10 to 12 mol % as a stabilizer and having an average particle diameter of 0.1 to 1 μm. The second phase includes an alumina particle deameter of 0.1 to 0.5 μm. However, in a case that the cerium oxide is used as a stabilizer, since the cerium oxide itself has a yellowish appearance, the color tone after sintering also comes to be yellowish a little. Therefore, when it is used as a dental prosthesis whose color is basically white, there arises a problem that the aesthetic property is poor.

As a conventional coloring method of zirconia, a method of adding metal oxide as a colorant, such as chromium oxide, nickel oxide, cobalt oxide, vanadium oxide or the like, according to a desired color tone, mixing them and sintering the mixture has been widely used (for example, refer to Japanese Patent Application Laid-Open Nos. 2005-306678 and 2004-059374). However, in this method, since thermal expansion coefficient and elastic modulus of the metal oxide used as a colorant are different from those of zirconia, a thermal stress and a residual stress are generated on a contact interface between a zirconia particle and the metal oxide at a time of sintering, so that pores and cracks are generated inside crystals of the obtained zirconia sintered compact. So, there is a problem that toughness and corrosion resistance are lacked, decreasing the strength is caused, or the like. Furthermore, since an operation of adding the metal oxide to the zirconia powder and mixing them are carried out in a powdery state, homogeneous dispersing is hard and color unevenness is easily caused.

Thus, as a method capable of coloring homogeneously and accurately by an easy process while maintaining mechanical and physical properties, a method of dipping a zirconia molded product in a liquid solution obtained by dissolving a color metal, impregnating the coloring metal into the zirconia formed product, and sintering them has been disclosed (for example, refer to Japanese Translation of PCT International Application Nos. 2002-536280 and 2010-534245). Japanese Translation of PCT International Application No. 2010-534245 discloses a method of using a solution containing at least one kind of salts or complexes of rare earth elements or subgroup elements having a specific concentration, and coloring translucent ceramics in a porous or absorbent state.

However, since the ceria-based partially stabilized zirconia is strongly yellowish. So, even when the formed product is dipped in the conventional a liquid solution obtained by dissolving a color metal so as to be impregnated with the coloring metal, the formed product is hardly colored to white. Therefore, a ceria-based partially stabilized zirconia material having a color tone suitable to be used as a dental prosthesis has been desired.

SUMMARY OF THE INVENTION

An objective of the present invention is to provide a zirconia-based composite ceramic sintered compact capable of being colored to white appropriate for a dental prosthesis while maintaining its mechanical and physical properties, and also provide a method for producing the same.

Present inventors carried out earnest works to solve the aforementioned problems and, as a result, they found the following to complete the present invention. That is, a zirconia-alumina composite ceramic, which includes an alumina particle and a zirconia particle comprising of tetragonal zirconia containing ceria of 8 to 12 mol %, is semi-sintered and then formed. After being dipped in a neodymium ion solution or complex solution and dried, the zirconia-alumina composite ceramic is finally sintered. Accordingly, even if a cerium oxide is used as a stabilizer for zirconia to make a yellowish appearance, a coloring liquid contains neodymium developing blue, so that a white zirconia-based composite ceramic sintered compact appropriate for a dental prosthesis can be easily obtained, maintaining its mechanical and physical properties.

Namely, according to an aspect of the present invention, a method for producing a zirconia-based composite ceramic sintered compact includes semi-sintering a zirconia-alumina composite ceramic containing an alumina particle and a zirconia particle comprising of tetragonal zirconia containing ceria of 8 to 12 mol %, forming the composite ceramic, dipping the formed composite ceramic in a neodymium ion solution or complex solution, drying the dipped composite ceramic, and then finally sintering it.

The method for producing a zirconia-based composite ceramic sintered compact according to the present invention can produce a zirconia-based composite ceramic sintered compact being colored to white appropriate to be used as a dental prosthesis while maintaining its mechanical and physical properties.

DETAILED DESCRIPTION OF PREFERRED EMBODIMENT

A zirconia-based composite ceramic used in the present invention contains an alumina particle and a zirconia particle comprising of tetragonal zirconia containing ceria of 8 to 12 mol %, and is obtained by pressing a powder of a raw material compound by CIP or the like and semi-sintering it. It is preferable that a treatment temperature in a semi-sintering processing is 900° C. or more to less than 1450° C. By setting the temperature in the semi-sintering processing within a range from 900° C. or more to less than 1450° C., decreasing a strength of a produced dental prosthesis can be prevented, and a time required for a cutting processing, which is a subsequent processing, can be shortened.

In the present invention, after the zirconia-based composite ceramics which is semi-sintered as mentioned above is cut to have a target shape by using CAD/CAM, the ceramics is dipped for 1 minute or longer in an neodymium ion solution or complex solution and dried, and then finally sintered. The neodymium ion solution or complex solution is produced by dissolving neodymium salts or complexes, more preferably chloride, acetates or a complex in a solvent such as water, alcohol or the like. It is preferable that the amount of ions or complexes is 2.5% by weight or more to 50% by weight or less. If the amount is less than 2.5% by weight or more than 50% by weight, the composite ceramics is hardly colored to white appropriate to be used as a dental prosthesis. More preferably, the amount is 2.5% by weight or more to 30% by weight or less.

The semi-sintered compact taken out from the neodymium ion solution or complex solution is dried and then finally sintered, so that a zirconia-alumina-based colored composite ceramic is produced. When such the produced zirconia-alumina-based colored composite ceramic is represented by L*a*b* color system, a value of L* is within a range from 85 or more to less than 100, a value of a* is within a range from −5 or more to 5 or less, and a value of b* is within a range from 0 or more to 10 or less. It is preferable that a measuring method of a color tone is according to JIS Z8722 2009, and a thickness of a sample piece is at least 2 mm or thicker.

The L*a*b* color system is to analyze the color tone with three factors of L* representing lightness (brightness), a* representing hue (the degree of red and green), and b* representing chroma (the degree of yellow and blue), and to express the color tone with three values of L*, a*, and b*. The value of L* representing lightness (brightness) is 85 or more to less than 100. If the value of L* is less than 85, the composite ceramic looks dark. More preferably, the value of L* is 88 or more to less than 94.

Further, the value of a* representing hue (the degree of red and green) is −5 or more to 5 or less. A reason of this is that if the value of a* is less than −5, green is too strong. As a result, when the reflected light irradiates the composite ceramic, the composite ceramic looks dark. If the value of a* is more than 5, redness is too strong. As a result, the composite ceramic looks rather unnaturally, so that it is not preferable. The more preferable value of a* is −5 or more to −2 or less.

Furthermore, the value of b* representing chroma (the degree of yellow and blue) is 0 or more to 10 or less. A reason of this is that if the value of b* is less than 0, blue is too strong, so that the composite ceramic looks dark. If the value of b* is more than 10, yellow is too strong, so that the effect of object of the present invention is hardly obtained. More preferably, the value of b* is 2 or more to 9 or less.

EXAMPLES

The present invention will be described in detail below based on examples. However, the present invention is not limited to these examples described below.

A powder of a raw material compound is prepared by the method in Japanese Patent No. 2945935. The powder of a raw material compound includes zirconium oxide of 65.9 to 69.9% by weight, cerium oxide of 10.1 to 11.1% by weight, aluminum oxide of 19.5 to 23.5% by weight, titanium oxide of 0.01 to 0.03% by weight and magnesium oxide of 0.04 to 0.08% by weight. A zirconia-based composite ceramic sintered compact was produced by pressing the prepared powder of a raw material compound to be a size of 10 mm×10 mm×8 mm; semi-sintering the pressed powder at 1000° C.; fully dipping the semi-sintered compact for two minutes at a room temperature in a solution illustrated in Table 1; and finally sintering the dipped compact at 1450° C.

The values of L*, a* and b* represented by L*a*b* color system of the produced zirconia-based composite ceramic sintered compact were measured by a measuring method according to JIS Z8722 2009 and a spectral photometry device (product name: CM3610d, produced by KONICA MINOLTA HOLDINGS, INC). These results were illustrated in Table 1.

TABLE 1

|  |  |  | Example 1 | Example 2 | Example 3 | Example 4 | Example 5 | Comparative example 1 | Comparative example 2 | Comparative example 3 | Comparative example 4 | Comparative example 5 |
|---|---|---|---|---|---|---|---|---|---|---|---|---|
| Solutions | Solvent | Water | 47.4 | 40.9 | 40.2 | 36.5 | 24.0 | 49.2 | 48.3 | 50.0 | 49.5 | 47.5 |
|  |  | Propylene glycol | 47.4 | 40.8 | 40.2 | 36.5 | 24.0 | 49.1 | 48.2 | 50.0 | 49.5 | 47.5 |
|  | Neodymium salts or complexes | NdCl3 | 5.2 |  |  |  | 52.0 | 1.7 | 3.5 |  |  |  |
|  |  | Nd(OH)3/XH2O |  |  |  | 27.0 |  |  |  |  |  |  |
|  |  | Nd2(CO3)3/XH2O |  |  | 19.6 |  |  |  |  |  |  |  |
|  |  | Nd2(CO3)3/6H2O |  | 18.3 |  |  |  |  |  |  |  |  |
|  | Compound not containing | CoCl2 |  |  |  |  |  |  |  |  | 1.0 | 5.0 |

TABLE 1-continued

| | | Example 1 | Example 2 | Example 3 | Example 4 | Example 5 | Comparative example 1 | Comparative example 2 | Comparative example 3 | Comparative example 4 | Comparative example 5 |
|---|---|---|---|---|---|---|---|---|---|---|---|
| | neodymium Neodymium concentration in a solution (wt %) | 3 | 6 | 12 | 20 | 30 | 1 | 2 | 0 | 0 | 0 |
| L* | | 92.7 | 90.4 | 90.1 | 89.6 | 89.2 | 94.1 | 92.7 | 93.7 | 81.5 | 62.9 |
| a* | | −2.8 | −2.8 | −2.7 | −2.4 | −2.1 | −3.1 | −2.9 | −2.8 | −4.6 | −4.5 |
| b* | | 8.6 | 6.7 | 4.5 | 2.4 | 2.4 | 13.2 | 10.2 | 13.3 | 0.8 | −7.9 |

It was confirmed clearly from Table 1 that the sintered compact in examples in which a neodymium ion solution or complex solution is used as a coloring liquid has a color tone represented by L*a*b* system, wherein the value of L* was 85 or more to less than 100, the value of a* was −5 or more to 5 or less and the value of b* was 0 or more to less than 10.

On the other hand, in comparative examples 1 to 3 having a low neodymium concentration in the solution, the value of b* was too high, and the produced compact was strongly yellowish, so that a white color appropriate for a dental prosthesis could not be obtained. In comparative examples 4 and 5 treated with a solution of a compound other than neodymium, the value of L* was low, and an entire color tone was dark, so that a white color appropriate for a dental prosthesis could not be obtained.

What is claimed is:

1. A method of producing a zirconia-based composite ceramic sintered compact, comprising:
   pre-sintering a zirconia-alumina composite ceramic comprising an alumina particle and a zirconia particle, the zirconia particle comprising tetragonal zirconia and comprising 8 to 12 mol % of ceria;
   forming the pre-sintered composite ceramic;
   dipping the formed composite ceramic in a neodymium ion solution or neodymium complex solution;
   drying the dipped composite ceramic; and
   sintering the dried composite ceramic.

2. The method of claim 1, wherein a neodymium concentration in the neodymium ion solution or neodymium complex solution is 2.5% by weight or more to 50% by weight or less.

3. The method of claim 2, wherein a neodymium concentration in the neodymium ion solution or neodymium complex solution is 2.5% by weight or more to 30% by weight or less.

4. The method of claim 1, wherein a color of the zirconia-based composite ceramic sintered compact is, in a color tone represented by L*a*b* color system:
   the value of L* is 85 or more to less than 100;
   the value of a* is −5 or more to 5 or less; and
   the value of b* is 0 or more to 10 or less.

\* \* \* \* \*